(12) United States Patent
Snell et al.

(10) Patent No.: US 8,467,862 B2
(45) Date of Patent: Jun. 18, 2013

(54) SYSTEMS AND METHODS RELATED TO ST SEGMENT MONITORING BY AN IMPLANTABLE MEDICAL DEVICE

(75) Inventors: Jay Snell, Studio City, CA (US); Bing Zhu, San Jose, CA (US); Katie Hoberman, Winnetka, CA (US); Harish Krishnaswamy, Mountain View, CA (US)

(73) Assignee: PaceSetter, Inc., Sylmar, CA (US)

( * ) Notice: Subject to any disclaimer, the term of this patent is extended or adjusted under 35 U.S.C. 154(b) by 338 days.

(21) Appl. No.: 13/049,805

(22) Filed: Mar. 16, 2011

(65) Prior Publication Data
US 2011/0245699 A1 Oct. 6, 2011

Related U.S. Application Data

(60) Provisional application No. 61/319,173, filed on Mar. 30, 2010.

(51) Int. Cl.
*A61B 5/04* (2006.01)

(52) U.S. Cl.
USPC .......................................... 600/509; 600/516

(58) Field of Classification Search
USPC .................. 600/508–528; 607/4, 5, 9, 14
See application file for complete search history.

(56) References Cited

U.S. PATENT DOCUMENTS

| | | |
|---|---|---|
| 5,251,621 A | 10/1993 | Collins |
| 5,313,953 A | 5/1994 | Yomtov et al. |
| 5,388,578 A | 2/1995 | Yomtov et al. |
| 6,016,443 A | 1/2000 | Ekwall et al. |
| 6,021,350 A | 2/2000 | Mathson |
| 6,115,628 A | 9/2000 | Stadler et al. |
| 6,128,526 A | 10/2000 | Stadler et al. |
| 6,256,538 B1 | 7/2001 | Ekwall |
| 6,324,421 B1 | 11/2001 | Stadler et al. |

(Continued)

FOREIGN PATENT DOCUMENTS

| | | |
|---|---|---|
| EP | 1164933 B1 | 5/2006 |
| WO | 0057781 | 10/2000 |

(Continued)

OTHER PUBLICATIONS

Restriction Requirement, mailed Jan. 27, 2010—Related U.S. Appl. No. 11/852,004.

(Continued)

*Primary Examiner* — Christopher D Koharski
*Assistant Examiner* — Catherine Voorhees

(57) ABSTRACT

Cardiac activity is sensed over a plurality of heart beats defining a beat set. For each beat in the set, it is determined whether the beat is a non-classified beat (e.g., paced beat, a beat outside of a specified heart rate range or a PVC), or a classified beat. For each classified beat, it is determined whether the beat is a non-detect beat, a minor beat or a major beat. Counts of classified beats, non-classified beats, major beats, minor beats, and non-detect beats are maintained. The beat set is declared to be one of a non-classified set, a major set, a minor set or a non-detect set based on the relative counts of classified beats, non-classified beats, major beats, minor beats, and non-detect beats. Over a period of time, counts of beat-set types are maintained and entry into and exit from ST episodes are determined based on these beat-set counts.

21 Claims, 13 Drawing Sheets

U.S. PATENT DOCUMENTS

| | | |
|---|---|---|
| 6,937,899 B2 | 8/2005 | Sheldon et al. |
| 7,274,959 B1 | 9/2007 | Wang et al. |
| 7,460,900 B1 | 12/2008 | Gill et al. |
| 7,558,623 B2 | 7/2009 | Fischell et al. |
| 7,610,086 B1 | 10/2009 | Ke et al. |
| 7,725,171 B1 | 5/2010 | Zhu et al. |
| 7,769,436 B1 | 8/2010 | Boileau et al. |
| 2004/0215092 A1 | 10/2004 | Fischell et al. |
| 2005/0059897 A1 | 3/2005 | Snell et al. |
| 2005/0113705 A1 | 5/2005 | Fischell et al. |
| 2005/0137482 A1 | 6/2005 | Laitio et al. |
| 2005/0137483 A1* | 6/2005 | Fischell et al. ............ 600/509 |
| 2006/0009811 A1 | 1/2006 | Sheldon et al. |
| 2006/0116593 A1 | 6/2006 | Zhang et al. |
| 2006/0167517 A1 | 7/2006 | Gill et al. |
| 2006/0265020 A1 | 11/2006 | Fischell et al. |
| 2010/0241017 A1* | 9/2010 | Johnson et al. ............ 600/509 |

FOREIGN PATENT DOCUMENTS

| | | |
|---|---|---|
| WO | 03020366 A1 | 3/2003 |
| WO | 03020367 A1 | 3/2003 |
| WO | 2004047917 A1 | 6/2004 |

OTHER PUBLICATIONS

NonFinal Office Action, mailed May 7, 2010—Related U.S. Appl. No. 11/852,004.

* cited by examiner

| EGM ▶ | DATE | TIME | HEART RATE AT ONSET bpm | MAX ST SHIFT % (HR bpm) | DURATION M:S |
|---|---|---|---|---|---|
| 〰️ | Aug 18, 2009 | 5:47 am | 70 | −32(70) | 37:56 |
| 〰️ | Aug 10, 2009 | 4:27 pm | 70 | −23(70) | 44:32 |
| 〰️ | Jul 17, 2009 | 10:20 am | 70 | −41(70) | 36:02 |
| 〰️ | Jul 15, 2009 | 9:35 pm | 70 | −25(70) | 31:02 |
| 〰️ | Jun 28, 2009 | 8:37 am | 98 | −84(114) | 30:50 |

11 Total

EGMs appear for the 4 most recent episodes and the first episode collected since last cleared.

FIG. 14

SYSTEMS AND METHODS RELATED TO ST SEGMENT MONITORING BY AN IMPLANTABLE MEDICAL DEVICE

CROSS REFERENCE TO RELATED APPLICATIONS

This application claims the benefit of U.S. Provisional Patent Application Ser. No. 61/319,173, filed Mar. 30, 2010, titled "ST Monitoring."

FIELD OF THE INVENTION

The invention generally relates to implantable cardiac stimulation devices, such as pacemakers, implantable cardioverter/defibrillators (ICDs) or cardiac resynchronization therapy defibrillators (CRT-Ds) and, in particular, to techniques for monitoring electrical cardiac activity for episodes of irregularity using such devices.

BACKGROUND OF THE INVENTION

Myocardial infarction, commonly known as a heart attack, is one of the leading causes of mortality in the western world. Myocardial infarction occurs when the blood supply to part of the heart muscle is interrupted causing some of the heart cells to die. The coronary arteries supply the heart muscle with the oxygenated blood that the heart needs to function. When the coronary artery flow is restricted heart cells will not get the oxygen they need to function, and could die. As the myocardial cells die, the ability of the heart to pump blood throughout the body is impaired.

Early detection and prompt intervention of an acute myocardial infarction significantly improves the clinical outcome. The mean time from myocardial infarction symptom onset to arrival at a hospital for treatment is about 2.5 to 3 hours. Surveys and focus groups of heart patients, family members, and the public report that they thought the presenting symptoms were less dramatic then expected. Many patients take a "wait and see" approach until they are more certain of the symptoms significance. A large proportion of irreversible myocardial injury and fatal ventricular arrhythmias occur in the first several hours after closure of a coronary artery. The longer the time between closure of the artery and the treatment lead to further myocardial necrosis and worse clinical outcomes. Treatment could include a defibrillation shock if the patient has an irregular heart arrhythmia, medication to help dissolve blood clots and open a blocked coronary artery, or a stent placement to open the blocked coronary artery.

Ischemic heart disease, or myocardial ischemia, is a disorder caused by a critical coronary artery obstruction termed atherosclerotic coronary artery disease (CAD). Atherosclerosis occurs when fatty material and plaque buildup on the walls of the artery. The buildup narrows the artery and the blood flow is decreased potentially leading to myocardial infarction. Myocardial infarction is an acute form of ischemic heart disease. Myocardial ischemia may be temporary and reversible, or permanent and irreversible leading to myocardial infarction. Myocardial ischemia can be temporary when there is brief periods of coronary occlusions followed by reperfusion, possibly in situations when the coronary blockage is not significant enough during normal conditions but as demand increases, for example with exercise, the blockage could become significant until the demand returns to normal. This has been termed myocardial stunning. Reversible myocardial ischemia depends mostly on the amount of time the myocardial cells have been restricted of oxygen, the shorter the amount of time the better, from seconds to minutes. The damage becomes permanent and irreversible when the blockage is severe or the flow has been compromised for longer, from minutes to hours.

Diagnosis of myocardial ischemia prior to a heart attack is important for optimal disease management. Approximately 1.5 million Americans a year have a heart attack resulting from myocardial ischemia, of these approximately 500,000 are fatal. In one third of those patients, CAD is not diagnosed until after a heart attack occurs. Treating known CAD is beneficial. Coronary artery revascularization, such as angioplasty, coronary artery bypass graft (CABG), or stent placement, and other medical therapies, such as medication, significantly reduce the morbidity and mortality rates of this disease. Therefore, early detection and diagnosis of CAD is critical.

The diagnosis of CAD is difficult because in many cases the disease is not apparent until after the patient has had a heart attack. Some patients with CAD experience symptoms such as unstable angina while others have no symptoms at all. This disease occurs in a range of patients, both the young and old, women and men, and in patients with and without co-morbidities. There currently is not a uniformly accepted screening method for CAD but the most common forms of testing are treadmill, or stress testing, and for patients with moderate-to-high risk for CAD, a cardiac imaging study.

Myocardial ischemia results in electrophysiological changes that are detectable. Within seconds of the onset of myocardial ischemia, there are ventricular morphology changes, including ST segment changes, called an ST shift, which can be seen on a surface electrocardiography (EKG).

Myocardial ischemia impairs ventricular contraction and relaxation, therefore altering the ST segment. In general, the underlying cause of the ST shift is an altered ion transport across the myocardial cell membrane. Measuring the ST segment deviation on the surface EKG, usually using a caliber-based technique or automated system, is the most common clinical technique for diagnosis of myocardial ischemia.

Treadmill tests are used on patients with symptoms or signs of CAD and patients with significant risk of CAD. Surface EKG monitoring is used during treadmill tests to see if there are any morphology changes in the beat complex, such as ST changes, during exercise when the heart requires more oxygen. Another method for detecting myocardial ischemia is with long-term electrocardiography recording using a Holter EKG monitor.

Holter EKG monitoring can help in detecting both symptomatic and asymptomatic, or silent, myocardial ischemia and is fundamental for characterizing episodes in patients with suspected or documented CAD. Long-term monitoring is beneficial since studies have shown that some patients, particularly with angina, experience short myocardial episodes at night or in the morning. Therefore, these patients' treadmill tests are usually negative. Holter EKG monitoring may reveal ischemia in about 10% of those with a negative treadmill test. Holter EKG monitoring has also shown that episodes of subendocardial (occurring under the endocardial, the inner most layer of tissue, of the wall of the heart) ischemia have a typical circadian distribution with a first peak in the morning hours and a second peak in the afternoon. Many studies have indicated that ischemia, even transient ischemia, on Holter EKG monitoring are among the major predictors of cardiac events in patients.

Practical application of long-term monitoring for ST segment deviations have been limited, due in part to the inconvenience of Holter EKG monitoring and the prevalence of false-positive ST segment deviations because of noise, postural changes, and artifacts. Chronic ischemia monitoring would be very beneficial in documenting the reproducibility of the ischemic pattern since day-to-day episodes can be variable. In addition, early and reliable detection of myocardial ischemia would be clinically valuable if the result is an improvement of the time to treatment for patients.

Another approach to chronic monitoring of the ST segment deviations is to use intracardiac electrograms (IEGMs) that are recorded by permanently implanted electrodes used in pacemakers and implantable cardioverter defibrillator (ICD) devices. IEGMs avoid the insulating effects of the lungs and thorax due to the distance between the electrodes, giving a five to 10 times larger signal amplitude then a surface EKG. Noise and signal artifacts are also greatly reduced due to the lack of electrode-skin interfaces. The location of the implanted electrodes is convenient, consistent, permanent, and capable of continuously monitoring of the ST segment using the IEGM. Indication for an ICD implant generally revolves around patients having or being ask risk for ventricular arrhythmias and about 50% of ICD patients either have documented CAD or are at risk of developing CAD. Several studies have shown that cardiac ischemia can be detected from IEGM of an ICD and that the sensitivity of IEGM for detection of ischemia may be superior to that of surface EKG. Another advantage of using implanted cardiac rhythm management devices is the ability to correlate ST segment changes with other cardiac events, such as ventricular arrhythmias.

The immediate benefit of chronic ST segment monitoring is the early confirmation of an acute coronary event or acute myocardial infarction in patients who have an implanted device. A second benefit is the potential to notify patients upon detection of a significant coronary event. This could greatly decrease the amount of time between ischemia onset and treatment. Additionally, the monitoring of the ST segment provides the possibility of early intervention that could positively affect clinical outcomes in CAD patients who have changes in their ischemia profile over the course of their disease.

SUMMARY OF THE INVENTION

Briefly, and in general terms, the invention relates to the monitoring ST segments. Electrical cardiac activity is sensed over a plurality of heartbeats defining a beat set. For each beat in the beat set, a determination is made as to whether the beat is a non-classified beat (e.g., a paced beat, a beat outside of a specified heart rate range or a PVC) or a classified beat. For each classified beat, a determination is made as to whether the beat is a non-detect beat, a minor beat or a major beat. Counts of classified beats, non-classified beats, major beats, minor beats, and non-detect beats are maintained. The beat set is declared to be one of a non-classified set, a major set, a minor set or a non-detect set based on the relative counts of classified beats, non-classified beats, major beats, minor beats, and non-detect beats. Over a period of time, counts of beat-set types are maintained and entry into and exit from ST episodes is determined based on these beat-set counts.

These and other aspects and advantages of the invention will become apparent from the following detailed description and the accompanying drawings that illustrate by way of example the features of the invention.

BRIEF DESCRIPTION OF THE DRAWINGS

The above and further features, advantages and benefits of the invention will be apparent upon consideration of the present description taken in conjunction with the accompanying drawings, in which:

FIG. 14 depicts an ST episode log maintained by the ST monitoring module; and

DETAILED DESCRIPTION OF THE PREFERRED EMBODIMENTS

In the following detailed description, reference is made to the accompanying drawings, which show by way of illustration specific embodiments in which the present invention may be practiced. These embodiments are described in sufficient detail to enable those skilled in the art to practice the invention, including using the best mode presently contemplated for such practice. It is understood that the embodiments may be combined or that other embodiments may be utilized, and that structural, logical, and electrical variations may be made without departing from the scope of the present invention. The following detailed description is, therefore, not to be taken in a limiting sense, and the scope of the present invention is defined by the appended claims and their equivalents. In this document, the terms "a" or "an" are used, as is common in patent documents, to include one or more than one; and the term "or" is used to refer to a nonexclusive or, unless otherwise indicated. Furthermore, like numerals or reference designators are used throughout to refer to like parts or elements.

Figure 1:
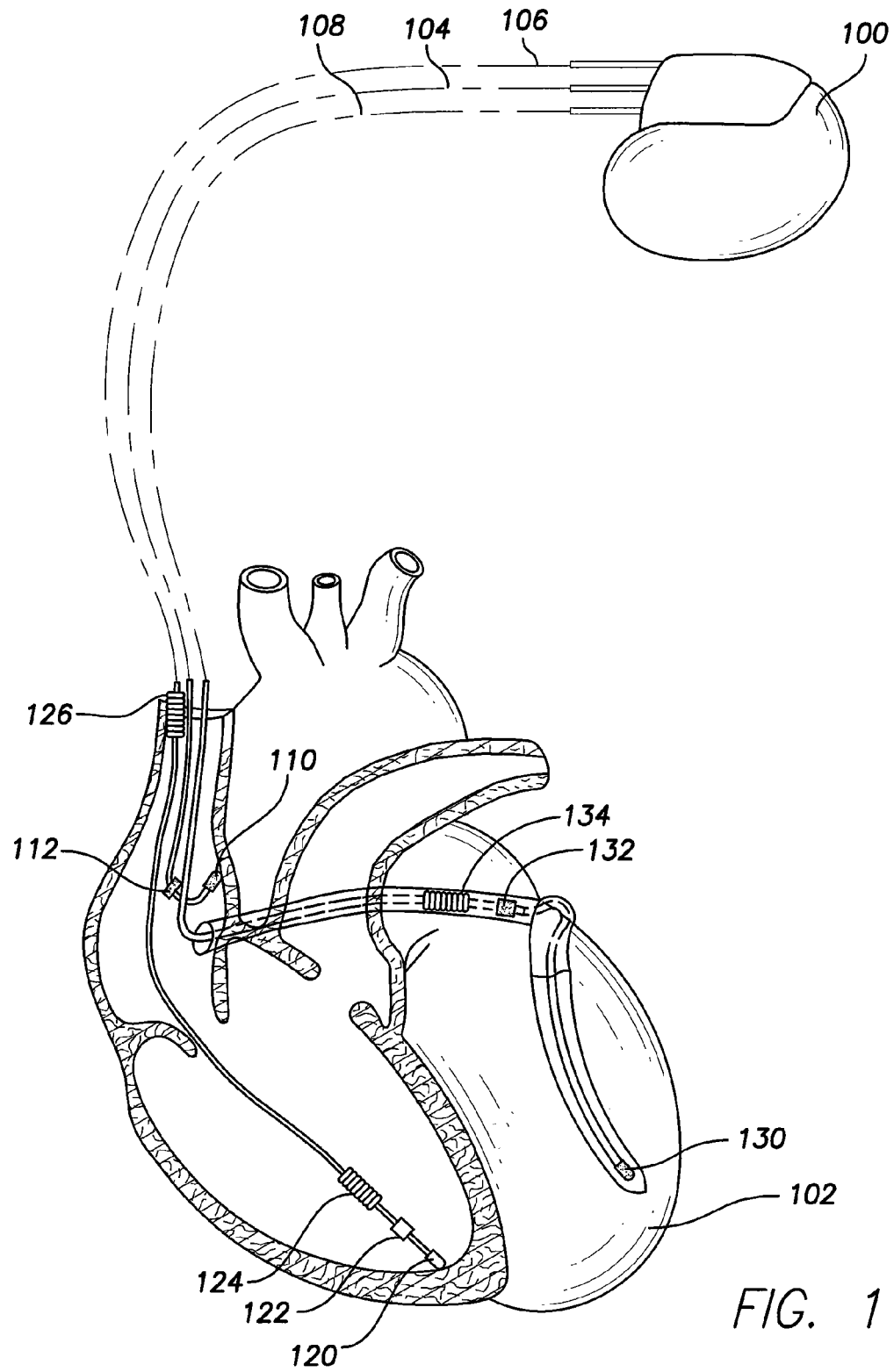
FIG. 1 is an illustration of a medical system including an implantable medical device (IMD) and a set of leads implanted in the heart of the patient.

The concepts described herein are intended for implementation in a medical system that is configured or configurable to delivery cardiac therapy and/or sense information germane to cardiac therapy. With reference to FIG. 1, one such medical system includes an implantable medical device (IMD) 100 and implantable leads 104, 106, 108 suitable for sensing cardiac activity and delivering multi-chamber therapy including cardioversion, defibrillation and pacing stimulation. The IMD 100 may be a cardiac pacemaker, an ICD, a defibrillator, an ICD coupled with a pacemaker, a cardiac resynchronization therapy (CRT) pacemaker, a cardiac resynchronization therapy defibrillator (CRT-D), and the like.

The IMD 100 is configured for placement in electrical communication with the right side of a patient's heart 102 by way of a right atrial (RA) lead 104 and a right ventricular (RV) lead 106. The RA lead 104 is designed for placement in a right atrium and, in this exemplary implementation, includes an atrial tip electrode 110, which typically is implanted in the patient's right atrial appendage, and an atrial ring electrode 112. Accordingly, the RA lead 104 is capable of sensing electrical cardiac signals, and delivering stimulation in the form of pacing therapy to the right side of the heart, and in particular the right atrium.

The RV lead 106, in this exemplary implementation, includes a RV tip electrode 120, a RV ring electrode 122, a RV coil electrode 124, and a superior vena cava (SVC) coil electrode 126. Typically, the RV lead 106 is designed to be transvenously inserted into the heart 102 to place the RV tip electrode 120 in the right ventricular apex, the RV coil electrode 124 in the right ventricle and the SVC coil electrode 126 in the superior vena cava. Accordingly, the RV lead 106 is capable of sensing electrical cardiac signals, and delivering stimulation in the form of pacing and shock therapy to the right side of the heart, and in particular the right ventricle.

The IMD 100 is in electrical communication with the left side of a patient's heart 102 by way of a coronary sinus (CS) lead 108 designed for placement in the coronary sinus region. As used herein the coronary sinus region refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The CS lead 108, in this exemplary implementation, includes a left ventricular (LV) tip electrode 130, a left atrial (LA) ring electrode 132, and a LA coil electrode 134. Typically the CS lead 108 is designed to be transvenously inserted into the heart 102 to access the coronary sinus region so as to place the LV tip electrode 130 adjacent to the left ventricle, the (LA) ring electrode 132 and the LA coil electrode 134 adjacent to the left atrium. Accordingly, the CS lead 106 is capable of sensing electrical cardiac signals, and delivering stimulation in the form of pacing and shock therapy to the left side of the heart.

Although three leads are shown in FIG. 1, fewer or more leads (with one or more pacing, sensing and/or shocking electrodes) may be used in order to efficiently and effectively provide pacing stimulation, cardioversion and/or defibrillation. Furthermore, an individual lead may include additional electrodes. For example, the coronary sinus lead 108 may include additional ring electrodes spaced apart between the tip electrode 130 and the coil electrode 134.

Figure 2:
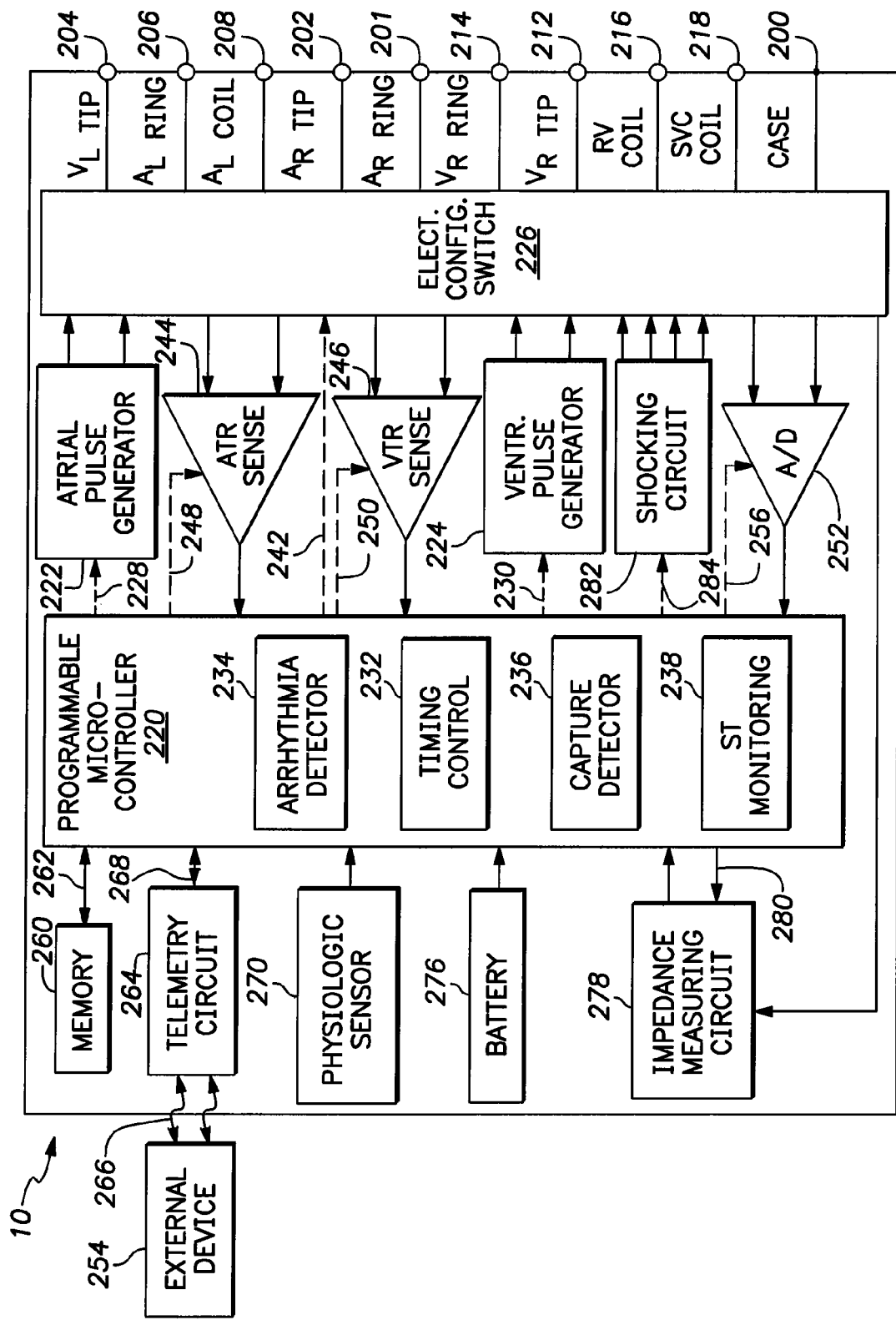
FIG. 2 is a functional block diagram of the IMD of FIG. 1, wherein the IMD is a pacer/ICD, illustrating basic circuit elements that provide cardioversion, defibrillation and/or pacing stimulation in the four chambers of the heart.

FIG. 2 shows an exemplary, simplified block diagram depicting various components of the IMD 100. The IMD 100 can be capable of treating both fast and slow arrhythmias with stimulation therapy, including cardioversion, defibrillation, and pacing stimulation. While a particular multi-chamber device is shown, it is understood that this is done only for illustration purposes. Thus, the techniques, methods, etc., described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

The housing 200 of the IMD 100 is often referred to as the "can", "case" or "case electrode", and may be programmably selected to act as the return electrode for all "unipolar" modes. The housing 200 may also be used as a return electrode alone or in combination with one or more of the coil electrodes 124, 126 and 134 for shock therapy delivery or other purposes. The housing 200 further includes a connector (not shown) having a plurality of terminals 201, 202, 204, 206, 208, 212, 214, 216, 218 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 110. A right atrial ring terminal ($A_R$ RING) 201 is adapted for connection to the atrial ring electrode 112. To achieve left chamber sensing, pacing, cardioversion and/or shocking stimulation, the connector includes at least a left ventricular tip terminal ($V_L$ TIP) 204, a left atrial ring terminal ($A_L$ RING) 206, and a left atrial shocking terminal ($A_L$ COIL) 208. These terminals are adapted for connection to the LV tip electrode 130, the LA ring electrode 132, and the LA coil electrode 134, respectively.

To support right chamber sensing, pacing, cardioversion and/or shocking stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218. These terminals are adapted for connection to the RV tip electrode 120, RV ring electrode 122, the RV coil electrode 124, and the SVC coil electrode 126, respectively.

At the core of the IMD 100 is a programmable microcontroller 220 that controls the various modes of cardiac sensing and therapy delivery. As is well known in the art, a microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, a microcontroller 220 includes the ability to process or monitor input signals (data or information) as controlled by a program code stored in a designated block of memory. The type of microcontroller is not critical to the described implementations. Rather, any suitable microcontroller 220 may be used that is capable of carrying out the functions described herein. The use of microprocessor-based control circuits for performing timing and data analysis functions are well known in the art.

With continued reference to FIG. 2, an atrial pulse generator 222 and a ventricular pulse generator 224 generate pacing stimulation pulses for delivery by the RA lead 104, the RV lead 106 and/or the CS lead 106 via an electrode configuration switch 226. It is understood that in order to provide stimulation therapy in each of the four chambers of the heart the atrial and ventricular pulse generators 222, 224 may include dedicated, independent pulse generators, multiplexed pulse generators, or shared pulse generators. The pulse generators 222, 224 are controlled by the microcontroller 220 via appropriate control signals 228, 230, respectively, to trigger or inhibit stimulation pulses.

An electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

An atrial sensing circuit 244 and a ventricular sensing circuit 246 may also be selectively coupled to the RA lead 104, the RV lead 106 and/or the CS lead 108 through the switch 226 for sensing electrical cardiac activity in each of the four chambers of the heart. Accordingly, the atrial sensing circuit 244 and ventricular sensing circuit 246 may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits 244, 246 are optionally capable of obtaining information indicative of tissue capture.

Each sensing circuit 244, 246 preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 100 to deal effectively with the difficult problem of sensing the low amplitude signal characteristics of atrial or ventricular fibrillation. The outputs of the atrial and ventricular sensing circuits 244, 246 are connected to the microcontroller 220, which in turn, is able to trigger or inhibit the atrial and ventricular pulse generators 222, 224, respectively, in a demand fashion in response to the absence or presence of cardiac activity in the appropriate chambers of the heart.

Sensed cardiac signals are also applied to inputs of an analog-to-digital (ND) data acquisition system 252. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the RA lead 104, the RV lead 106, and/or the CS lead 108 through the switch 226 to sample cardiac signals across any pair of desired electrodes. The A/D data acquisition system 252 is controlled by the microcontroller 220 through a control signal 256 that controls the transfer of data from the acquisition system to the microcontroller.

The microcontroller 220 includes timing control circuitry 232 operative to control the timing of the stimulation pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., all of which is well known in the art.

The microcontroller 220 also includes an arrhythmia detector 234 that employs one or more algorithms that process sensed cardiac activity to detect arrhythmias. Depending on the detected arrhythmia, the detector 234 may call for administration of one or more stimulation therapies. The detector 234 may be implemented in hardware as part of the microcontroller 220, or as software/firmware instructions programmed into the device and executed on the microcontroller 220 during certain modes of operation.

For arrhythmia detection, the IMD 100 may utilize the atrial and ventricular sensing circuits 244, 246 to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The arrhythmia detector module 234 uses timing intervals between sensed events (e.g., P-waves, R-waves, and depolarization signals associated with fibrillation which are sometimes referred to as "F-waves" or "Fib-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of therapy that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

The microcontroller 220 further includes a capture detection module 236 and an ST monitoring module 238. These modules implement various exemplary recognition algorithms and/or methods presented below. The aforementioned components may be implemented in hardware as part of the microcontroller 220, or as software/firmware instructions programmed into the device and executed on the microcontroller 220 during certain modes of operation.

The capture detection module 236 is capable of analyzing information output from the sensing circuits 244, 246 and/or the data acquisition system 252 to determine or detect whether and to what degree tissue capture has occurred and to program a pulse, or pulses, in response to such determinations. The sensing circuits 244, 246, in turn, receive control signals over signal lines 248, 250 from the microcontroller 220 for purposes of controlling the gain, threshold, polarization charge removal circuitry (not shown), and the timing of any blocking circuitry (not shown) coupled to the inputs of the sensing circuits 244, 246, as is known in the art.

The ST monitoring module 238 includes a diagnostic algorithm that monitors IEGMs for changes in ST segment measurements relative to one or more thresholds. One such ST segment measurement, referred to herein as an ST shift, is a measurement of the relative amplitude of a portion of a ventricular IEGM that includes an ST segment to a reference window measured immediately prior to the R wave of the IEGM.

ST segment monitoring involves periodic analysis of sets of cardiac beats contained within an IEGM. In one configuration, the analysis occurs between every 30 to 90 seconds. A set of cardiac beats consists of a predetermined number, e.g., 15, of intrinsic or paced ventricular complexes. A criterion of M out of N beats is used to determine if a ST shift occurs within the beat set being analyzed. In one embodiment, M=6 and N=8. For example, if six beats are measured as "shifted" before three "non-shifted" beats are analyzed the set is classified as "shifted". The algorithm waits until the next 30 to 90 second interval and re-evaluates the ventricular complexes. If a number, e.g. three, of consecutive "shifted" sets is detected, the algorithm considers this a ST episode. When a set is classified as "non-shifted," the algorithm waits 90 seconds before analyzing the next set. Once a set is classified as "shifted", the algorithm analyzes a set every 30 seconds.

In one configuration, two levels of ST episodes are detected based on the degree of ST-shift. These levels are referred to as minor ST episodes and major ST episodes. The distinction is made based on an ST-segment shift threshold that can be set independently as either a positive or a negative shift. The threshold is a predefined value that the ST-shift value needs to exceed to be considered either a minor shift or a major shift. There is also another type of minor ST episode called a persistent minor ST episode. If a minor ST episode is ongoing, meaning the ST-shift is greater than the minor threshold, for a period of time that exceeds a predefined "persistence time" the detection of a persistent minor ST episode is triggered. An ST episode is terminated when a number, e.g., two, of consecutive "non-shifted" beat sets occur.

ST-shifts can be determined because the current ST-segment being evaluated is compared to a baseline, non-shifted ST-segment. The algorithm performs baseline ST segment extraction once every six hours, called a time segment. A baseline set is a qualified reference of a patient's normal, non-shifted rhythm. This qualified reference is used to determine how the patient's current ST-shift deviates from the non-shifted rhythm. Baseline sets are averaged over the last three days and then are used to classify intervals in the same time segment, 24 hours later. If the signal shows a ST-shift when a baseline is attempted then the baseline cannot be extracted at that time and the algorithm waits until there is no ST-shift.

The microcontroller 220 is further coupled to a memory 260 by a suitable data/address bus 262, wherein the programmable operating parameters used by the microcontroller 220 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveform, number of pulses, and vector of each shocking pulse to be delivered to the patient's heart 102 within each respective tier of therapy. Other pacing parameters include base rate, rest rate and circadian base rate.

Advantageously, the operating parameters of the IMD 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the IMD 100, etc., as contained in the microcontroller 220 or memory 260) to be sent to the external device 254 through an established communication link 266.

The IMD 100 can further include one or more physiologic sensors 270. For example, the IMD 100 may include a "rate-responsive" sensor that may provide, for example, information to aid in adjustment of pacing stimulation rate according to the exercise state of the patient. However, the one or more physiological sensors 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the IMD 100, it is to be understood that one or more of the physiologic sensors 270 may also be external to the IMD, yet still be implanted within or carried by the patient. Examples of physiologic sensors that may be implemented in a device 100 include known sensors that, for example, sense oxygen content of blood, respiration rate, pH of blood, ventricular gradient, cardiac output, preload, afterload, contractility, and so forth. Multiple sensors 270 may be provided.

The IMD 100 additionally includes a battery 276 that provides operating power to all of the circuits shown in FIG. 1. For an IMD 100 that employs shocking therapy, the battery 276 is capable of operating at low current drains for long periods of time (e.g., preferably less than 10 μA) and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The IMD 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the IMD 100 is intended to operate as an implantable cardioverter/defibrillator (ICD) device, it detects the occurrence of an arrhythmia, and automatically applies an appropriate therapy to the heart aimed at terminating the detected arrhythmia. Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation.

To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the LA coil electrode 134, the RV coil electrode 124, and/or the SVC coil electrode 126. As noted above, the housing 200 may act as an active electrode in combination with the RV coil electrode 124, or as part of a split electrical vector using the SVC coil electrode 126 or the LA coil electrode 134 (i.e., using the RV electrode as a common electrode).

Figure 3:
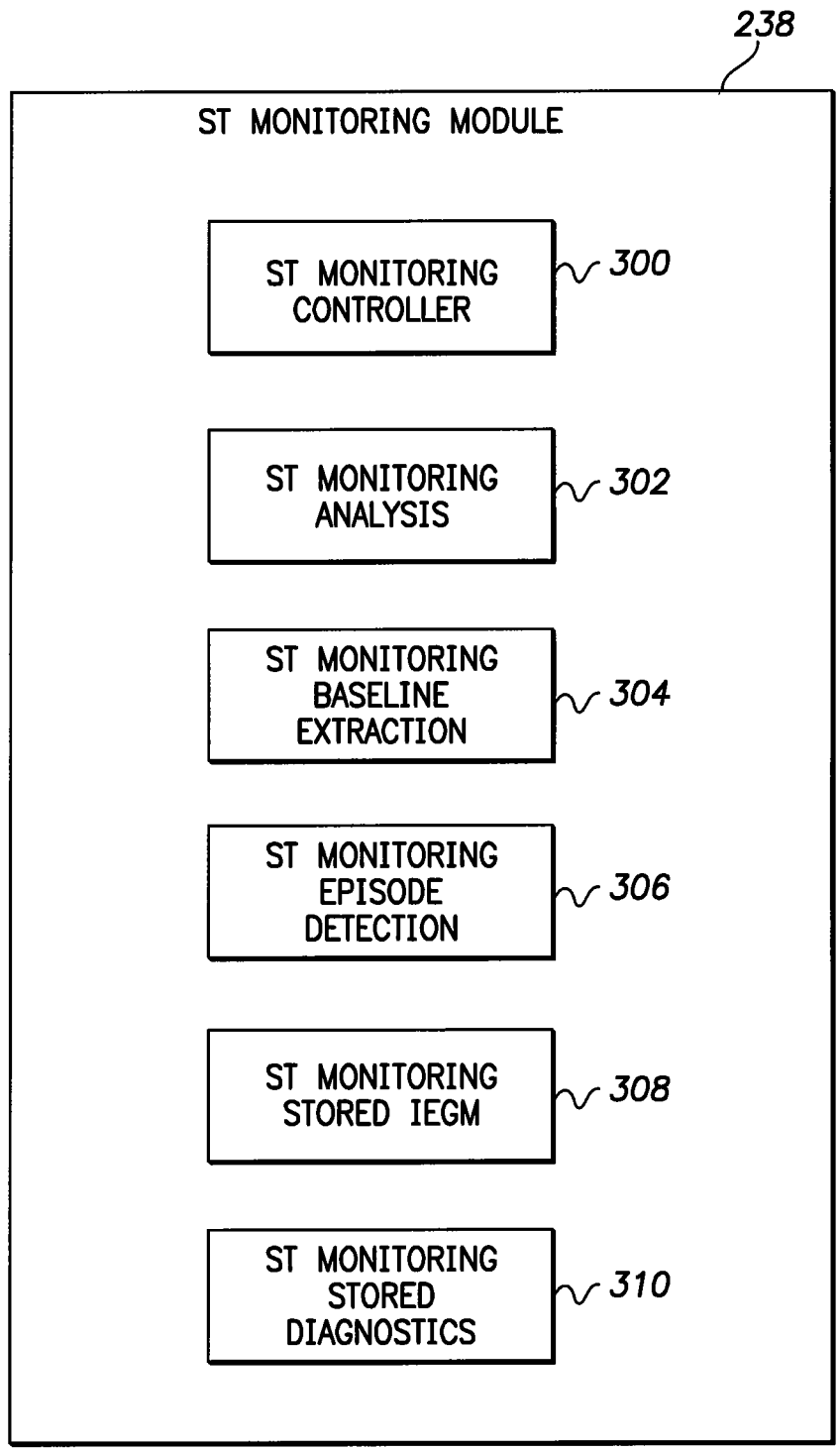
FIG. 3 is a functional block diagram of the ST monitoring module of FIG. 2.

With reference to FIG. 3, the ST monitoring module 238 includes: a ST monitoring controller module 300 that initializes the overall ST monitoring algorithm and controls when ST analysis is performed; a ST monitoring analysis module 302 that does complex analysis and determines when a beat set is complete; a ST monitoring baseline extraction module 304 that extracts the non-shifted baseline set; and a ST monitoring episode detection module 306 that determines the entry/exit criteria for a ST episode. The ST monitoring module 238 also includes a ST monitoring stored IEGM module 308 that collects IEGM signals for diagnostics and a ST monitoring stored diagnostics module 310 that stores diagnostic data including ST-Segment data, baseline data, and ST episode data. Each of these modules is described further below, wherein the ST monitoring module 238 is at times referred to as the "ST monitoring algorithm" or "ST monitoring system".

ST Monitoring Controller

The ST monitoring controller module 300 controls when ST monitoring activity can occur based on the state of the device. The controller module 300 controls the high-level operation of the ST monitoring algorithm 238. It dictates when beat set analysis should begin and handles interactions with other features in the device. For example, the controller module 300 handles the timers related to the beat search interval, tachyarrhythmia pause, and hourly timer. The search interval timer is the 30 or 90 second separation between when beat sets are analyzed. The tachyarrhythmia pause is a timer that is started when a shock therapy is delivered to the patient. The controller 300 will not allow a beat set to be analyzed for a period after a shock is delivered. The hourly timer keeps track of hours, days, and weeks for the rest of the ST monitoring system 238.

Figure 4:
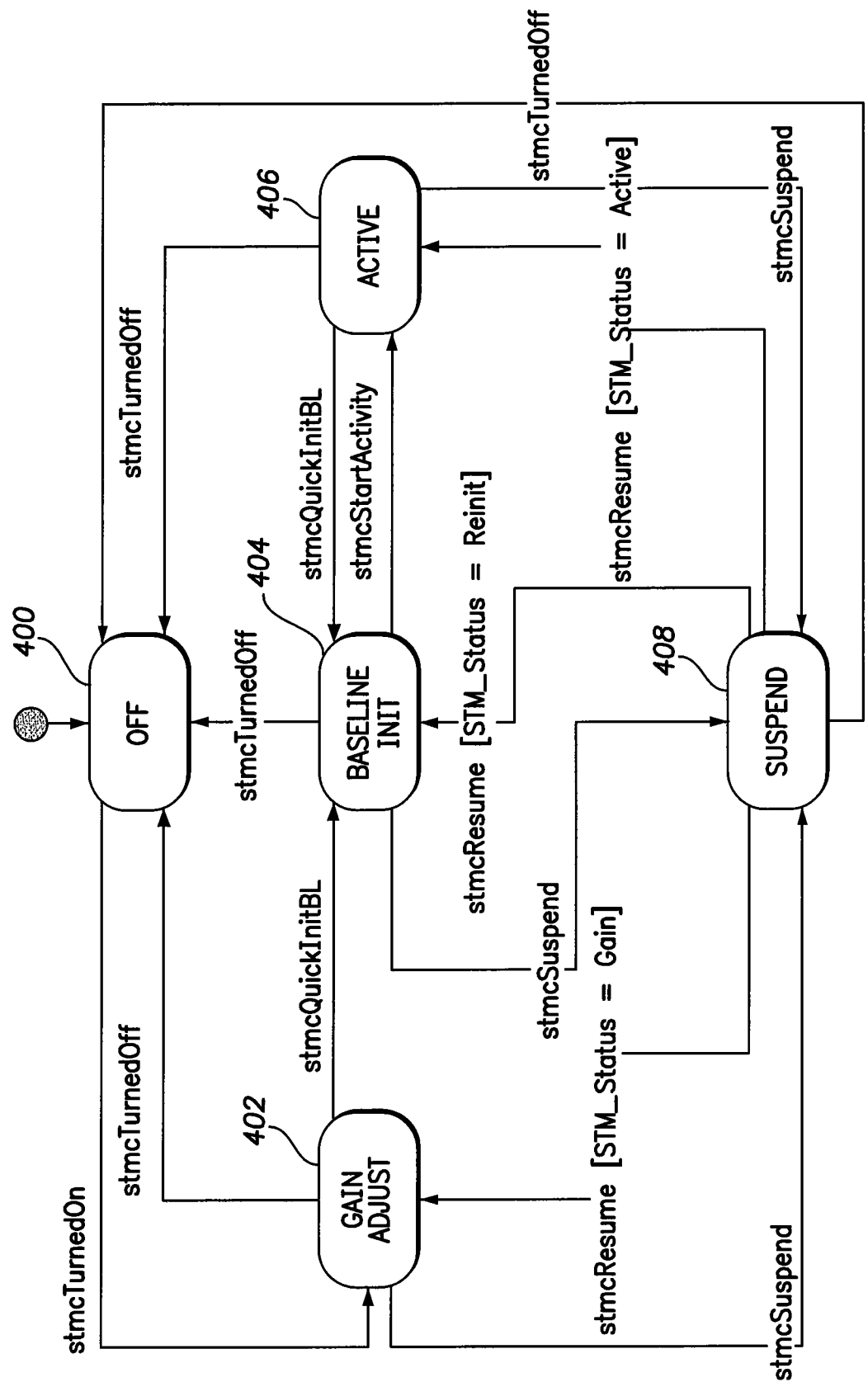
FIG. 4 is a state diagram related to the operation of the ST monitoring module.

With reference to FIG. 4, the ST monitoring algorithm 238 has four states that are represented in a status variable including off 400, gain adjustment 402, quick initialization (also called baseline initialization) 404, and active 406. When the ST monitoring algorithm 238 is programmed off the status is off 400. When the ST monitoring module 238 is attempting to set the gain the status is gain adjustment 402. When new baselines need to be calculated the status is quick initialization 404; and when the ST monitoring algorithm 238 is in normal operation of analyzing sets and detecting episodes the status is active 406.

Based on the state of the ST monitoring algorithm 238 certain activities are allowed. Once the ST monitoring algorithm 238 is turned on, the gain value for the dedicated hardware channel is determined. Once the gain is determined, a baseline is extracted through a quick-initialization process. This process can also occur at other times during device lifetime. ST episode detection is not allowed during quick-initialization. After gain 402 and baseline initialization 404 are completed the ST monitoring algorithm 238 is considered active 406. While in an active state, the ST monitoring algorithm 238 performs cardiac beat set analysis at regular intervals. Anytime ST monitoring is ongoing it may be suspended 408, due to interactions with other parts of the system, where all beat-set analysis is ended until the suspension is removed.

Figure 5:
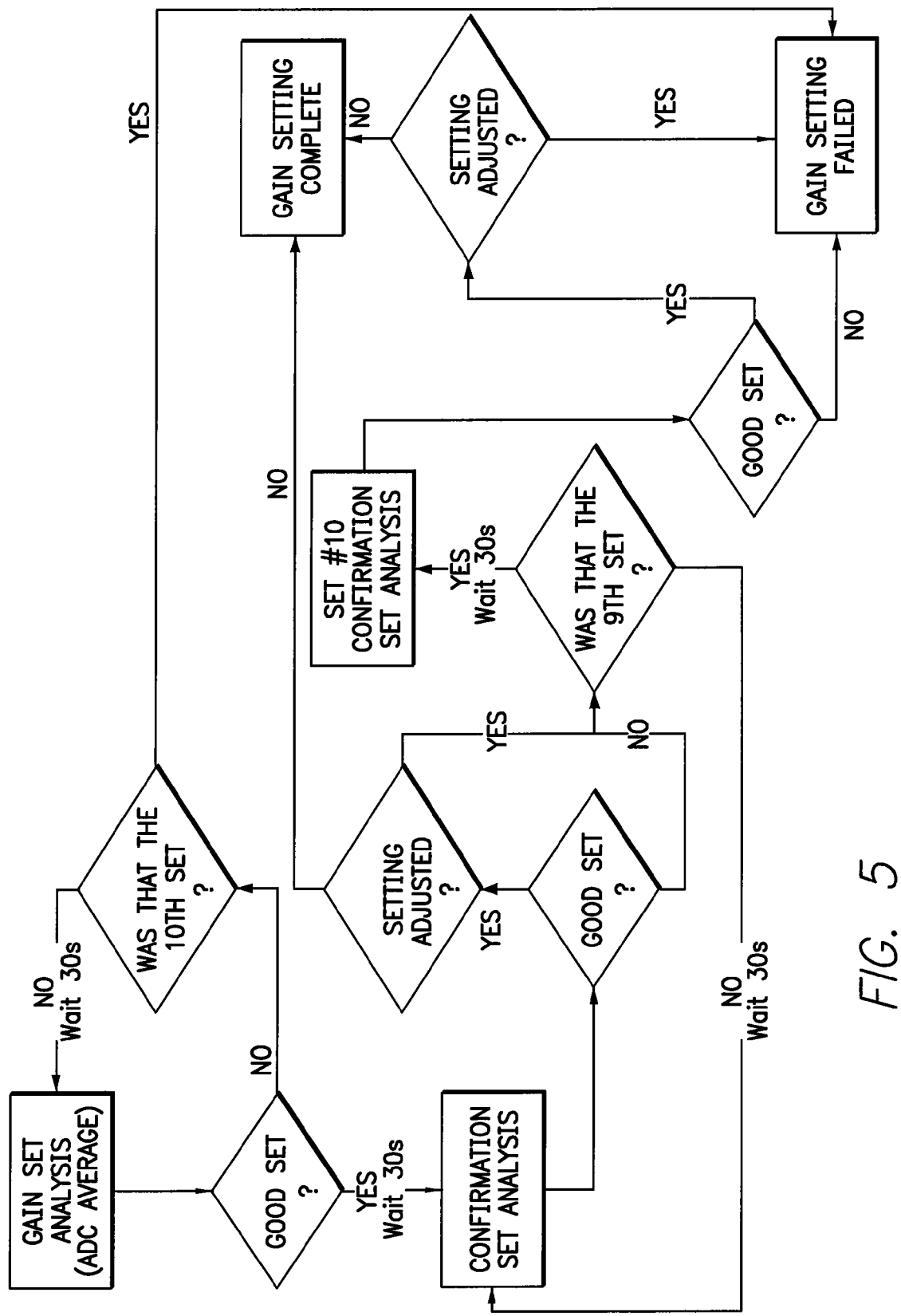
FIG. 5 is a flow chart related to the gain selection function of the ST monitoring module.

With reference to FIG. 5, the controller 300 sets a fixed gain value for the dedicated hardware channel where ST segments are analyzed when the algorithm is toggled to ON. This is because the ST deviation (the difference between an ST segment and PQ segment) and ST shift (difference between a current ST deviation and a baseline ST deviation) values are done in ADC (analog to digital converter) counts and the voltage value that each ADC count correlates to is needed for diagnostic purposes. Selecting the optimal gain for each patient provides calculations that are more precise. The algorithm characterizes up to 10 beat sets an hour. Each hour begins with the highest available gain setting and consists of two steps, selection and confirmation. Upon successful completion of these two steps the gain adjustment for the algorithm is considered successful.

Gain selection uses functionality of the ST monitoring analysis module 302 (described in detail below) to determine if a gain set is good based on a count criteria such as 6 good beats within 15 total beats. A good beat is an intrinsic ventricular event, or R wave, that is not a premature ventricular contraction (PVC). A PVC is an intrinsic ventricular event that occurred too soon, as determined by the current ventricular interval compared against a percentage of the pre-set interval average criteria (explained in the next section). A bad beat is a ventricular-paced event or PVC. Gain sets are analyzed every 30 seconds. Using the 6 good beats in a gain set, the average R peak ADC value is calculated. This calculated ADC value is then used—in conjunction with the following look-up table—to determine the appropriate full-scale gain setting for the channel.

| Averaged R-Peak ADC count of the Gain Set (absolute value) | Gain Setting (mv) | Gain Index |
| --- | --- | --- |
| 53-107 | 78.2 | 9 |
| 43-52 | 38.2 | 8 |
| 28-42 | 31.3 | 7 |
| 22-27 | 19.9 | 6 |
| 15-21 | 16 | 5 |
| 10-14 | 10.2 | 4 |
| 8-9 | 7.1 | 3 |
| 5-7 | 5.2 | 2 |
| 4-4 | 3.6 | 1 |
| 0-3 | 2.4 | 0 |

The algorithm has up to 10 sets to select and confirm the gain selection every hour. Once a gain setting has been selected, a subsequent beat set is used to confirm the selected gain setting. To confirm the gain setting, the average R peak of the 6 good beats should fall within 40-85% of the gain setting. Both non-gain sets and sets that do not confirm the gain settings are regarded as a failed set and contribute to the 10 set total required to finalize the gain. This value is used to convert the ADC values of the R wave amplitudes and ST segment values to millivolt values for the diagnostic display. Optimizing the gain value on the hardware provides better resolution of the signal based on each patient's R wave.

Figure 6:
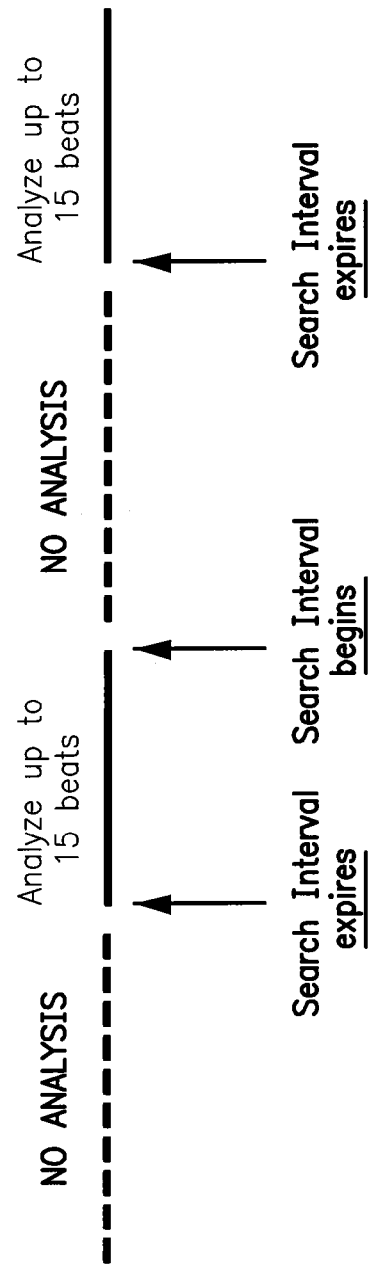
FIG. 6 depicts alternating periods of search intervals and beat analysis.

With reference to FIG. 6, the ST monitoring algorithm 238 does not perform true continuous analysis. To simulate continuous monitoring the algorithm 238 conducts an analysis every 30 or 90 seconds, called a search interval. The controller 300 has a timer manager that controls the search-interval timer and determines whether to load 30 or 90 seconds. Depending on the state of the ST monitoring algorithm 238, the search interval could be fast or slow. The actual value is programmable but usually 30 and 90 seconds between sets respectively. The 30-second interval is used when the ST monitoring algorithm 238 is doing gain adjustment or in an ST episode, otherwise the 90-second interval is used. When the search interval expires a set can be analyzed and when analysis is complete a new search interval is started.

The timer manager also controls a one hour timer which is started on the programming of the ST monitoring algorithm 238 from OFF to ON. The timer is stopped when the algorithm is programmed from ON to OFF. This timer functions to keep track of hours, days, and months, for diagnostics and baseline extraction purposes.

The controller 300 also handles critical interactions with the rest of the system 238. These critical interactions are recognized as features that may prevent ST monitoring analysis from being reliable. An example of such a feature or interaction is ventricular arrhythmias and therapy delivery. When these interactions are ongoing, the controller 300 suspends most ST monitoring activities, including beat set analysis and ST episode detection. Some critical interactions terminate any ongoing ST episodes. Diagnostics, however, are allowed to be stored during suspension. Once the critical interaction is removed or not ongoing, the controller 300 restarts the search interval timer so ST analysis may resume.

ST Monitoring Analysis

Figure 7:
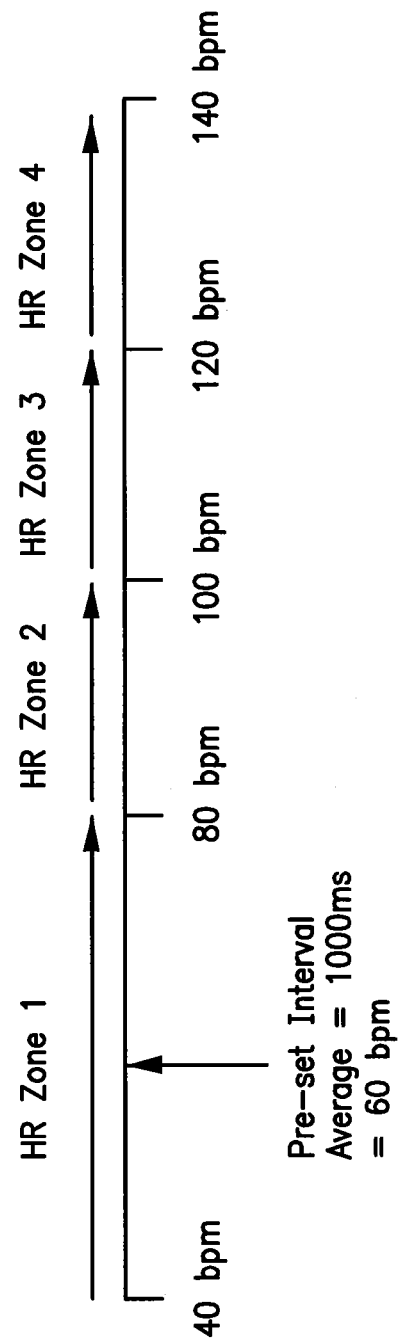
FIG. 7 depicts exemplary heart rate zones employed by the ST monitoring module to determine whether a beat satisfies a good-beat criteria.

The ST monitoring analysis module 302 conducts beat-to-beat complex analysis of ST segments and determines the characterization of a beat set. ST segment analysis is conducted on beats that meet a good beat criteria. With reference to FIG. 7, a good beat is an intrinsic, non-PVC beat within one of four defined heart rate zones. All other beats, including PVC beats, paced beats, and out-of-range beats, are considered bad beats and are characterized as non-classified. There are four heart rate zones, each with their own parameters for analyzing a beat because as the heart rate increases the morphology and duration of ST segments may change. The zone a beat set belongs to is determined by the ventricular interval when the set begins, called the pre-set interval average.

Figure 8:
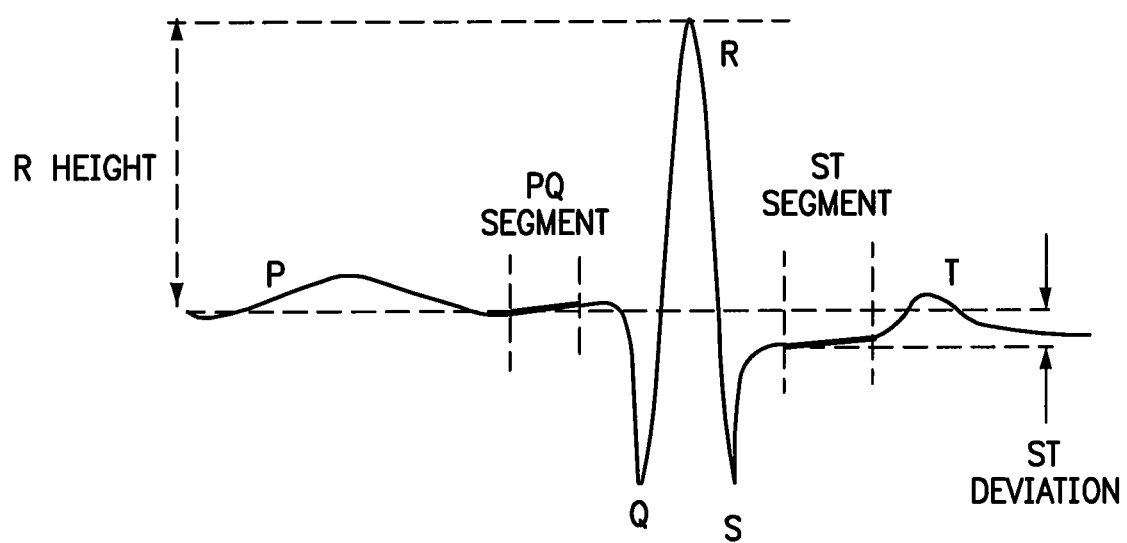
FIG. 8 depicts the morphology of a heart beat.
Figure 9:
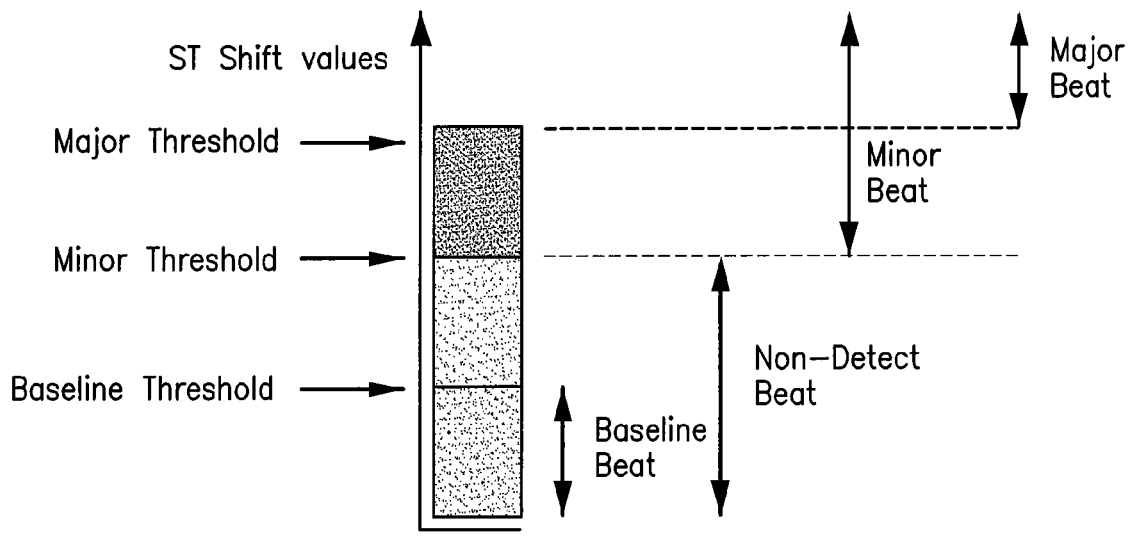
FIG. 9 depicts the various thresholds used to characterize a heart beat.

Once a beat is determined to be a good beat, the morphology of the beat is analyzed to calculate an iso-electric (or PQ segment) value, R peak value, and ST segment value in absolute ADC counts. With reference to FIG. 8, the ST deviation for the beat is the difference between the beat's ST segment and the PQ segment. The ST shift for the beat is the difference between the beat's ST deviation and the current baseline ST deviation. With reference to FIG. 9, the ST shift value is then compared against threshold values to determine if this is a non-detect (or baseline if baseline extraction is ongoing), major, or minor beat.

The ST monitoring system recommends values for major and minor thresholds based on histogram ST deviation data collected for each day up to seven days. These histograms are the histograms for which there would have been no alarm for the patients (that is this histogram is collected for the patient's day when he did not have an ST episode).

$$\text{Standard Deviation} = \sqrt{\frac{n \times \sum x^2 - (\sum x)^2}{n \times (n-1)}} \quad \text{Equation (2)}$$

Equation (1) is a derivation of equation (2). Equation (2) is the standard formula for standard deviation=spread. The reason equation (2) converted into equation (1) is that the data set for equation (1) is in histogram format while for equation (2) the data is as it is and is not in histogram format conventionally.

After calculating the weighted standard deviation for seven days, it is multiplied by an empirically determined number selectable in the algorithm from 2.0 to 5.0 in increments of 1. This weighted spread multiplied by this empirically determined number is called the Pos_Spread and Neg_Spread. All the ST deviation data, i.e., $RPQ_{base}$ base, collected for each day is averaged over 24 hours and then the $RPQ_{base}$ is weighted averaged over 7 days. Thus, the ST deviation is normalized to the R height.

Recommended positive and negative major thresholds from this 7 days of data are determined by 1) calculating the mean of each heart rate bin (A0, A1, A2 and A3) for each day; 2) for each heart rate bin calculate the weighted average over the seven days (the reason for weighted average being the same as explained above); 3) for each heart rate bin calculate the maximum among the 15 days day-to-day difference (mean_day1-mean_day2, mean_day2-mean_day3 and so on) in mean; 4) similarly calculate the minimum (minimum because there are negative values involved) of day to day mean difference for the negative major threshold recommendation; and 5) use the following formula to calculate the recommended positive and negative major thresholds.

$$\text{rec\_pos\_thr(bin)} = \text{MAX}\left(0, INT\left[1 + 100 \times \left(\frac{\text{mean(bin)} - \text{mean}(A0) + \text{pos\_spread} + \text{pos\_mean\_delt(bin)} + 5}{RPQ_{base}}\right)\right]\right)$$

$$\text{rec\_neg\_thr(bin)} = \text{MAX}\left(0, INT\left[1 - 100 \times \left(\frac{\text{mean(bin)} - \text{mean}(A0) + \text{neg\_spread} + \text{neg\_mean\_delt(bin)} - 5}{RPQ_{base}}\right)\right]\right)$$

There are four bins A0, A1, A2, and A3, each corresponding to a different heart-rate range. Assume that bin A0 would have the max number of beats at any given time because this would have the heart rate beat for normal functioning of the patient (e.g., everyday life situation and no exercise or physical exertion). For bin A0, the spread=standard deviation for the ST deviation data in the bin is calculated. The division of the spread=standard deviation into positive and negative spread is done because it is assumed that there will be inherent imbalance in number of beats falling in negative standard deviation bin to the positive deviation bin, i.e. the distribution will not be symmetrical.

For bin A0 after calculating spread=standard deviation for each of the seven days, a weighted average of these seven standard deviations is calculated. This brings each days beat numbers into the picture to account for standard deviation having greater number of beats for individual days.

$$\text{pos\_sigma(day)} = \sqrt{\frac{A_>}{n_> - 1}} \quad \text{Equation (1)}$$

The minor threshold is a percentage of the major threshold. In one configuration, the percentage is fixed at 2% of the R peak below the major threshold. For example, if the major threshold recommendation of 22% and −18% is accepted the minor threshold will be 20% and −16% respectively.

Figure 10:
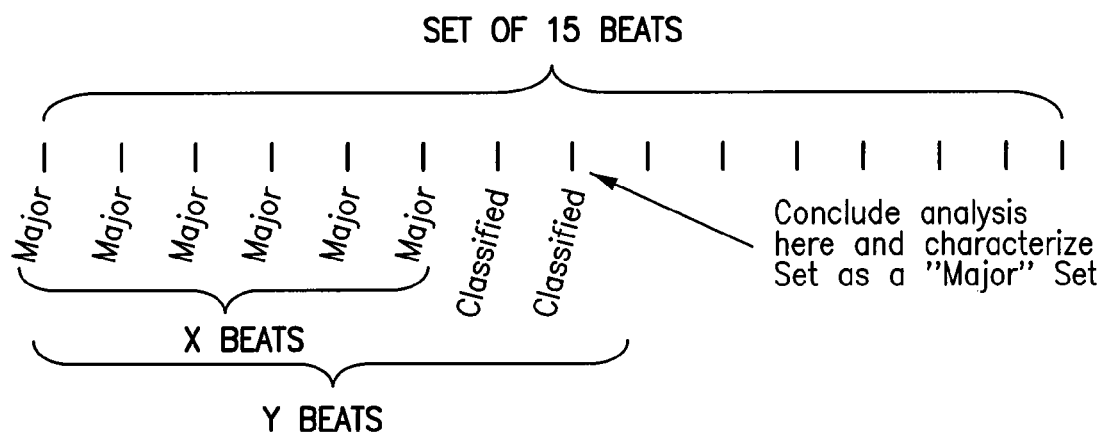
FIG. 10 depicts a count criteria used to classify a set of heartbeats.

With reference to FIG. 10, the ST monitoring analysis module 302 uses a X of Y criteria to characterize each good beat as classified (major, minor, non-detect) and each bad beat as non-classified until one of the following beat set criteria is met for either major, minor, non-detect or non-classified. The ST monitoring analysis module 302 employs two levels of racing counters. One counter maintains counts between classified and non-classified beats, while the other counter maintains counts amongst major, minor and non-detect beats. Both race conditions for the respective counters are designed such that only one beat category can conceivably be the winner in each race. Between classified and non-classified beats, the race condition stipulates that a win occurs within a fixed window of a preset number of beats. In one embodiment the number is 15 beats, which means either classified reaching its programmable threshold of Y (nominally 8) or non-classified reaching 15−Y+1 shall be declared the winner. Between major, minor and non-detect the race condition may occur within the subset of Y classified beats. Similarly the stipulation states that either major or minor reaching a threshold of X (e.g., nominally 6 in the 15 beat embodiment) beats or non-detect reaching Y−X+1 within Y classified beats shall be declared the winner.

ST Monitoring Baseline Extraction

The ST monitoring baseline extraction module 304 periodically obtain baseline sets. A baseline set is a qualified reference of the patient's normal, non-shifted rhythm. This qualified reference is used to determine how the patient's current ST shift deviates from the non-shifted rhythm. Every six hours, the ST monitoring baseline extraction module 304 attempts to extract a reference ST segment during normal heart rhythm activity. Sets of up to 15 beats are analyzed and characterized in a way similar to the way beat sets are characterized by the ST monitoring analysis module 302. The ST monitoring baseline extraction module 304 classifies each beat as a baseline beat, or a non-baseline beat. The extraction succeeds and a beat set is characterized as a baseline set if it contains an acceptable number of baseline beats. Baseline beats are based on good beats qualified by the ST monitoring analysis module 302. In order for a good beat to be a baseline beat, it should meet the following criteria: ventricular sensed event, rate within heart rate zone one, non-saturated R peak measurement, ST shift is less than 50% of the major ST thresholds, and ST shift is less than the minor ST thresholds (see FIG. 9). The R-peak value is a measure of the amplitude of an R-wave. The R-wave peak value is used to scale the ST thresholds of an extracted baseline set. The process of evaluating the magnitude of ST deviation is performed by the ST monitoring analysis module 302.

The ST monitoring baseline extraction module 304 updates the major and minor thresholds and the reference ST segment for the current time segment. There are four, six-hour time segments in one twenty-four hour day, and each of these segments has its own threshold and ST Segment reference values for the ST monitoring analysis module 302 to use when characterizing sets. At the beginning of a new time segment, the most recent baseline set from the appropriate time segment is used to calculate the major and minor thresholds. Baseline extraction could be unsuccessful for the following reasons: calculated shift is above the baseline threshold, heart rate is out of heart rate zone 1, analyzed beats are non-classified, and R waves are saturated. Baseline extraction is not attempted when an ST episode is ongoing or a critical interaction prevents analysis. Baseline extraction attempts to characterize a baseline set up to 10 times each hour for a given six hour time segment until a successful baseline is extracted.

There are times when the ST monitoring algorithm 238 resets the baseline values, called quick initialization 404 (FIG. 4). During quick initialization 404 the baseline ST segment value is reset to zero and the R peak value is reset to max which resets all threshold values. Alternatively, a quick initialization 404 can reset the ST segment to the voltage detected when the algorithm was first activated. Then extraction of new baselines is attempted. Quick initialization 404 occurs after the gain has been selected, when a successful baseline has not been detected for three days, and when the iso-electric or ST parameters associated with heart rate zone 1 are reprogrammed. Again, during quick initialization 404 ST episodes cannot be detected. Once a successful baseline is extracted, the thresholds are recalculated and the algorithm enters the active state 406.

ST Monitoring Episode Detection

The ST monitoring episode detection module 306 determines the times at which a patient has entered into or exited from an ST episode. An ST episode is a ventricular rhythm that contains an ST shift above one of the programmed ST thresholds. Depending on the threshold that is crossed by the shift, and the duration it remains above the threshold, and heart rate zone, an ST episode may be diagnosed as a major episode, a minor episode, or persistent minor episode.

The ST monitoring episode detection module 306 detects ST episode entry and exit. Entry into an episode is detected after the ST monitoring analysis module 302 characterizes a series of beats to be a major or minor set. If a minor set persists past an adjustable duration, entry into a persistent minor episode is detected. Exit out of an episode is determined after the ST monitoring analysis module 302 characterizes a consecutive number of sets as non-detect or non-classified past an adjustable criteria.

When the ST monitoring episode detection module 306 receives a new characterized set, it updates a group of bins as specified in the following set behavior table.

| Set Characterization | Major Set Bin | Minor Set Bin | Non-Detect Bin | Non-Classified Set Bin (outside an episode) | Non-Classified Set Bin (during an episode) |
|---|---|---|---|---|---|
| Major | Count | Count | Initialize = reset count to zero | No Change | Initialize |
| Minor | No Change | Count | Initialize | No Change | Initialize |
| Non-Detect | Initialize | Initialize | Count | No Change | Initialize |
| Non-Classified | No Change | No Change | No Change | Count | Count |

The behavior table dictates how the major, minor, non-detect, and non-classified bins are updated. To enter a major/minor ST episode, a consecutive number of major/minor sets must occur (nominally three) separated by two or fewer non-classified sets are required. A single non-detect set breaks the chain of consecutive major/minor sets used for detection. Each time one of these bins is updated, the episode entry and exit detection rules are checked. When the bin count for major or minor reaches three, entry into that type of episode occurs. When the bin count for non-classified sets reaches a specified number (nominally three) or the bin count for non-detect sets reaches a specified number (nominally two) the ongoing ST episode is exited. ST episodes can also be exited if three days have elapsed since the entry of the episode or due to certain critical interactions. Baseline extraction is suspended when an ST episode is ongoing.

ST Monitoring Stored Intracardiac Electrograms

ST monitoring stored IEGM module 308 provides IEGM data, markers and timestamps to be retrieved and displayed on an external instrument so that a clinician can examine the ST Segment variations. When an ST episode occurs the IEGM module 308 stores IEGM data for baseline sets and specific sets. The four most recent successful baseline sets and the four most recent unsuccessful baseline sets are stored. When an ST episode is detected the IEGM data of the baseline set that was referenced by ST monitoring analysis module 302 to determine the ST shift is saved as well as the entry set and the set that contains the maximum ST shift during the ST episode.

ST Monitoring Stored Diagnostics

Figure 11:
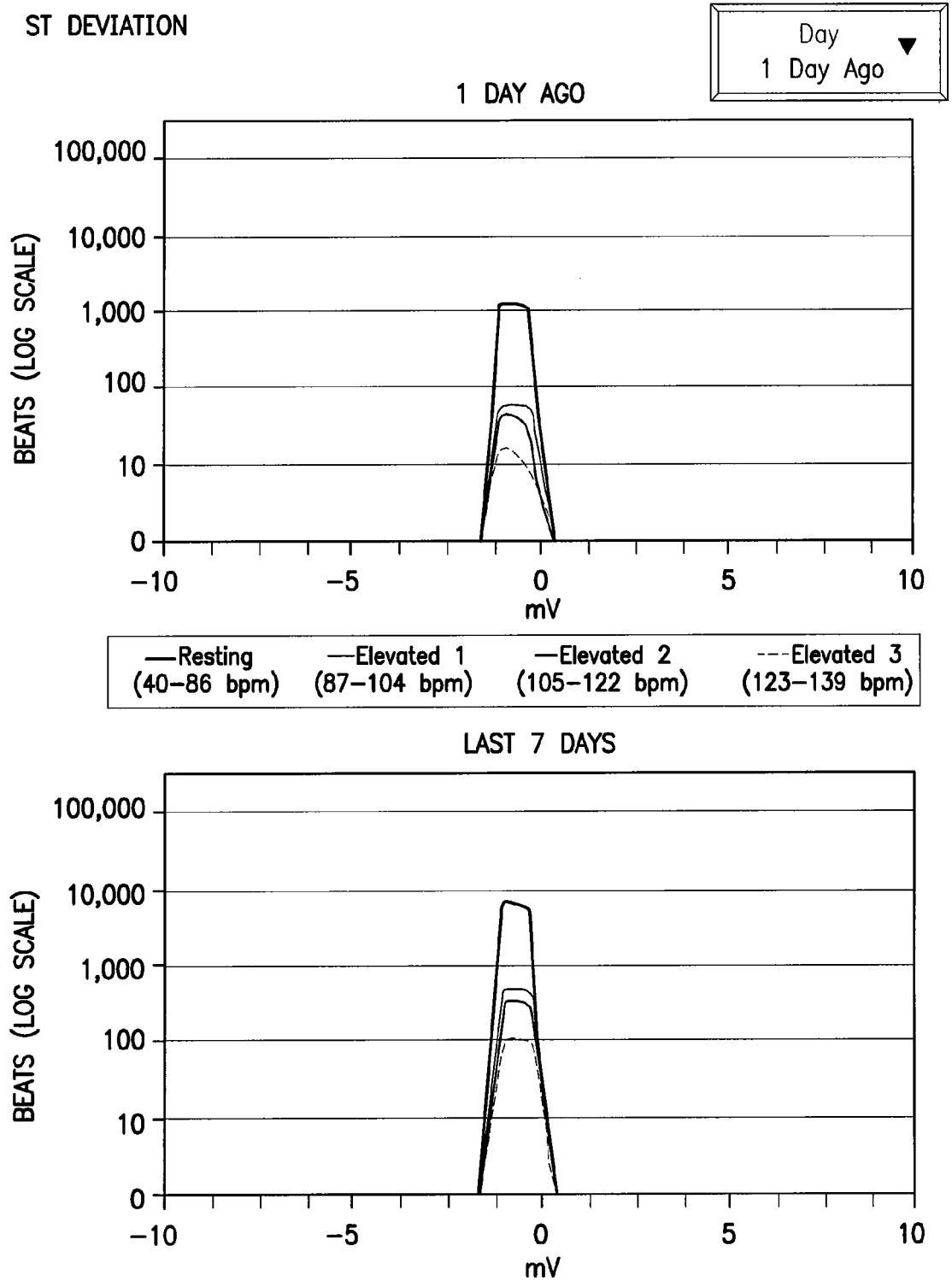
FIG. 11 depicts diagnostic histograms maintained by the ST monitoring module.

The IEGM data is part of the diagnostics gathered by the ST monitoring module 238. The module 238 collects many diagnostics intended to help a physician make informed decisions as a patients disease progresses. For example, the ST monitoring module 238 collects data on ST deviations. With reference to FIG. 11, every single ST deviation the algorithm calculates is stored into a daily histogram that consists of bins with a specified ST deviation range for each heart rate zone for each day. After the ST deviation is determined for a good beat the histogram bin that corresponds to the day, heart rate zone, and ST deviation value for this beat is incremented by one. ST deviation from the most recent seven days is also stored.

Figure 12:
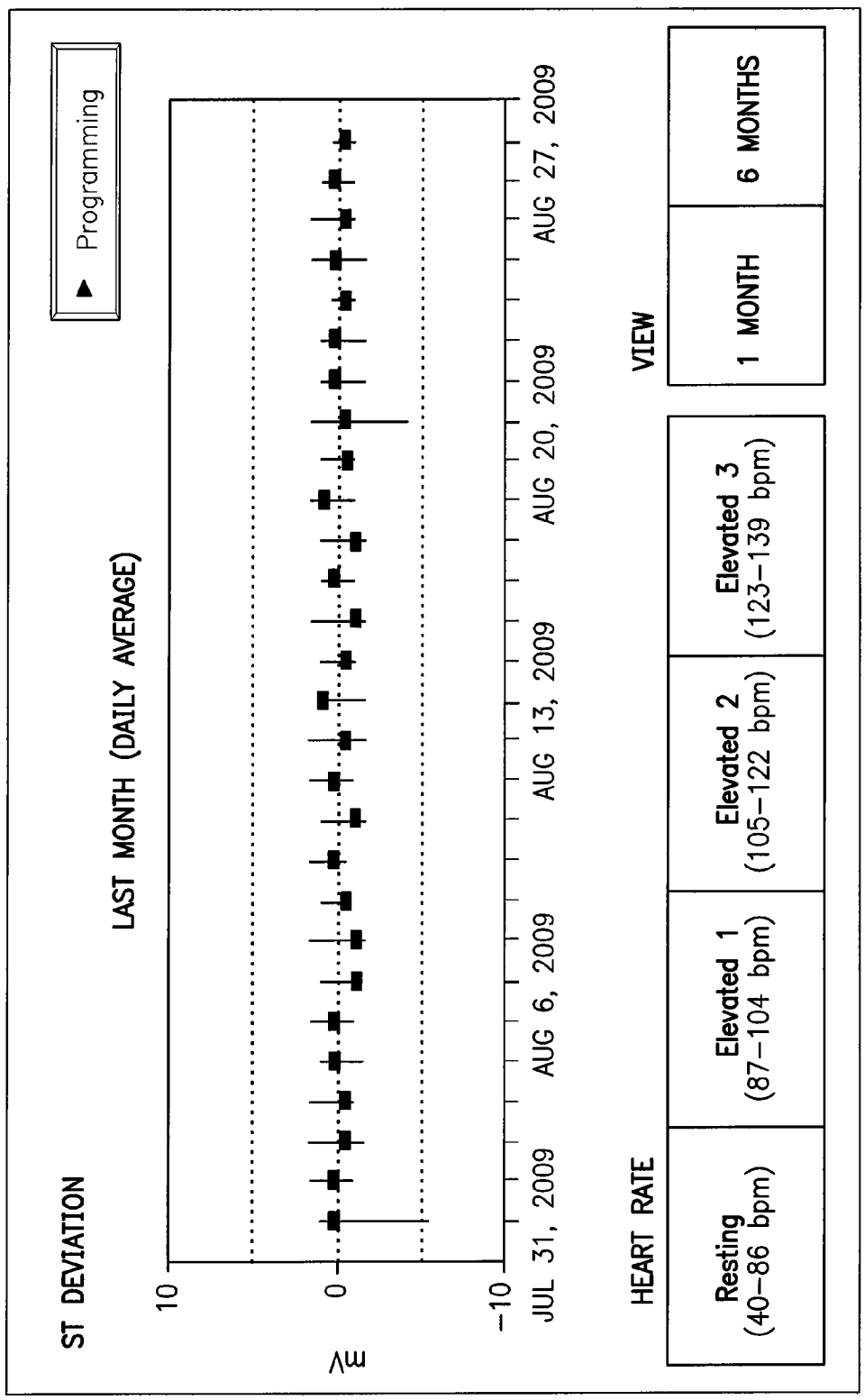
FIG. 12 depicts a weekly trend for ST deviation maintained by the ST monitoring module.

At the end of each 24-hour period, or day, an ST deviation daily trend is updated. The daily trend holds the minimum, maximum, and mode (most frequent) ST deviation from the current day for each heart rate zone. Again, there are seven days of trend data stored. As shown in FIG. 12, similarly there is a ST deviation weekly trend that holds the minimum, maximum, and mode ST Deviations for each heart rate zone for the week. The weekly trend holds up to six months of data.

Figure 13:
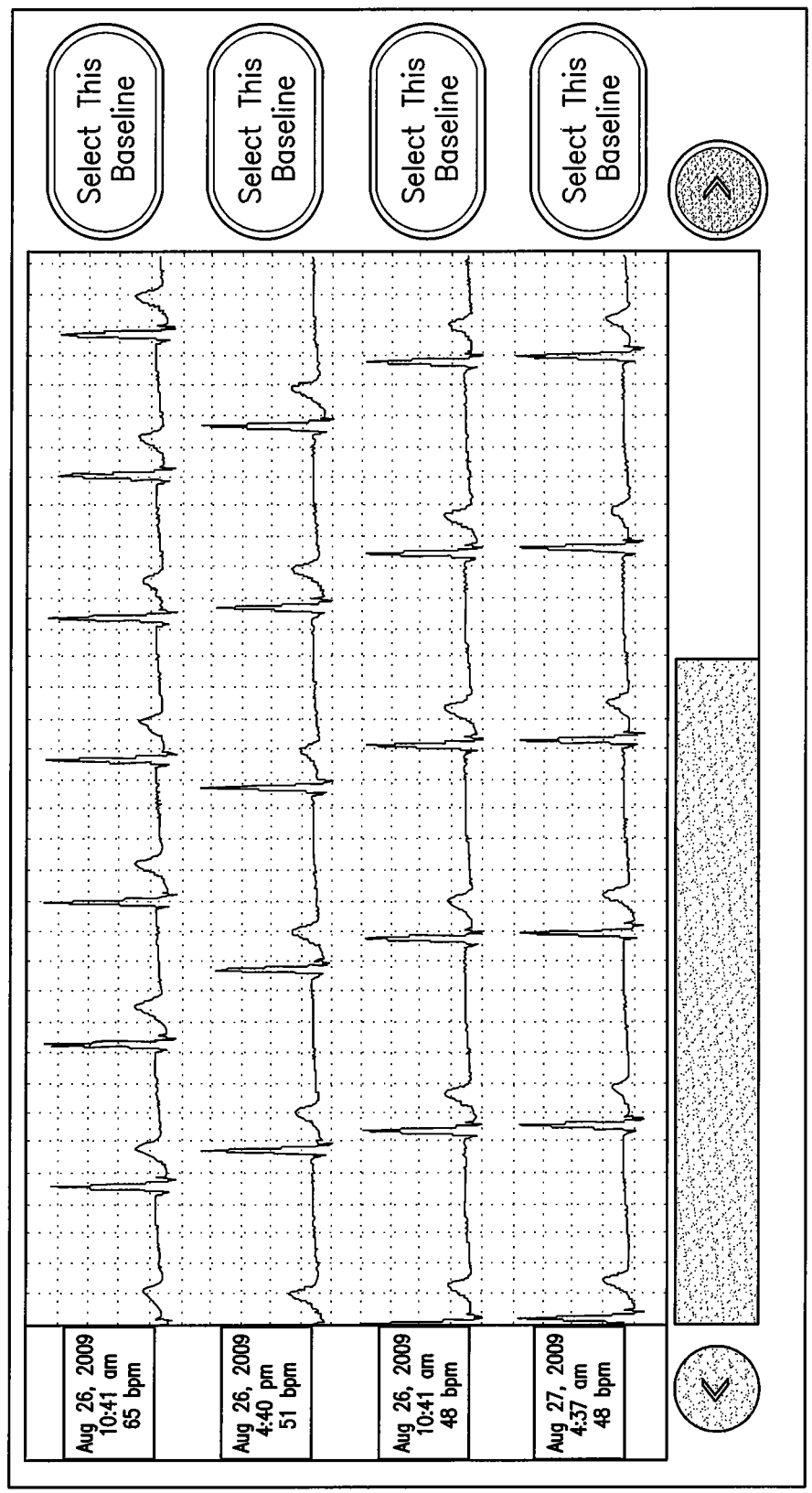
FIG. 13 depicts ST baseline IEGM data maintained by the ST monitoring module.

The ST monitoring module 238 also stored diagnostics associated with the baseline sets that are extracted. With reference to FIG. 13, the baseline diagnostics available on a display are associated with the four baselines, one for each six-hour time segment, which include the IEGM data as well as the average ST deviation and average R peak for the baseline set. The research diagnostics that are collected by the device are the four most recent unsuccessful baselines diagnostic, the unsuccessful baseline failure reason counters, the raw baseline log, the quick-initialization counter, and the paced set diagnostics. The unsuccessful baseline diagnostic includes the IEGM data and failure reason for the most recent four unsuccessful baseline extractions. The reasons for failure listed in the unsuccessful baseline diagnostic also have counters. The device keeps track of how many times a baseline fails for one of four reasons, excess shift, high heart rate zone, saturated R waves, and non-classified beats. Baseline extraction could fail due to a high ST shift or a high heart rate. In addition, if the R wave amplitude value is too high or too low the baseline extraction will fail.

Another diagnostic associated with baselines is the raw baseline log. The result of baseline extraction for each time segment for the last 100 days is stored. When a baseline set is extracted for a segment the timestamp, ST deviation, and R peak of the successful baseline is stored. If baseline extraction is unsuccessful for a segment the timestamp, ST deviation, and R peak are stored for the set that was the first attempt of the segment. If baseline extraction was not allowed for a segment, possibly due to an interaction or ST episode ongoing, then the log is updated with a timestamp and values that indicate there was no baseline extraction attempted.

The last of the research diagnostics are the quick-initialization counter and the paced set diagnostics. The quick-initialization counter is updated every time quick-initialization occurs. The paced set diagnostics is a 100-day log. Each entry represents a day and holds the total number of sets analyzed and the number of those sets that included at least one paced event.

Figure 15:
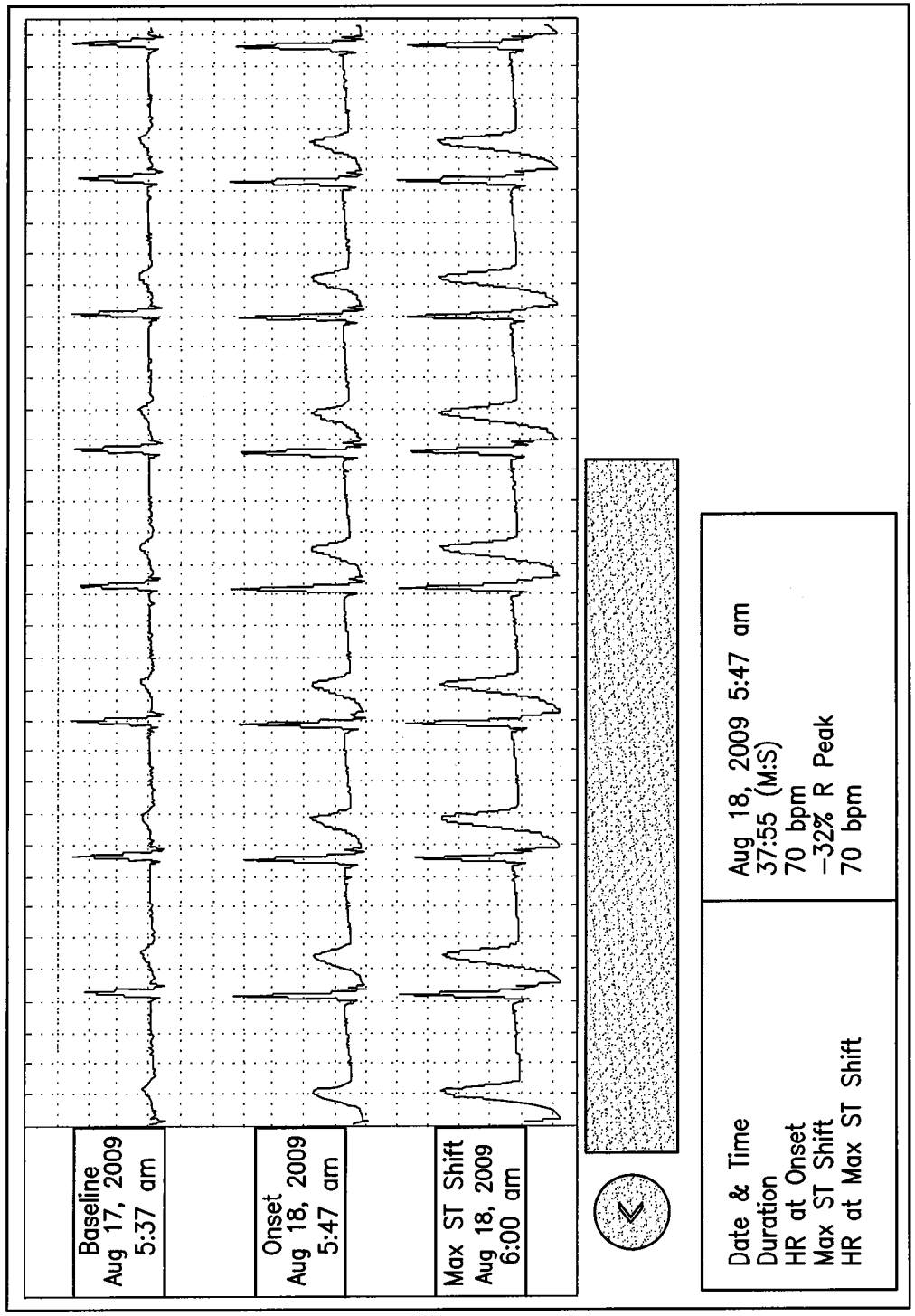
FIG. 15 depicts IEGMs and other data corresponding to ST episode detection, maintained by the ST monitoring module.

With reference to FIG. 14, the ST monitoring module 238 also stores diagnostics associated with ST episodes. There are three ST episode logs, major episode, persistent minor episode, and minor episode. Each log holds the same type of information. There is a counter for the total number of ST episodes for that type. There is a timestamp for when the ST episode was entered and exited, which is used to calculate the duration of the ST episode. The interval average of the rhythm prior to the entry set and the average ST shift of the entry set are recorded. The average R peak of the reference baseline set that was used to determine the ST shift is recorded. The interval average of the rhythm prior to the set with the max ST shift and the average ST shift of the set with the max ST shift are recorded. Lastly the reason for the episode to exit is recorded, including non-detect sets detected, non-classified sets detected, critical interaction terminated, episode exceeded three days, or minor/persistent minor exited due to major ST episode detected. As shown in FIG. 15, each ST episode has three sets of IEGM data associated with it, the reference baseline data, the entry set data, and the max ST Shift set data.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting. Many other embodiments will be apparent to those of skill in the art upon reviewing the above description. The scope of the invention should therefore be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of monitoring ST segments, said method comprising:
    sensing electrical cardiac activity over a plurality of heart beats defining a beat set;
    for each beat in the beat set, determining whether the beat of the ST segment is a non-classified beat or a classified beat;
    for each classified beat, determining whether the beat is a non-detect beat, a minor beat or a major beat;
    maintaining a count of classified beats, a count of non-classified beats, a count of major beats, a count of minor beats, and a count of non-detect beats;
    declaring the beat set to be one of a non-classified set, a major set, a minor set or a non-detect set based on the relative counts of classified beats, non-classified beats, major beats, minor beats, and non-detect beats.

2. The method of claim 1 wherein determining whether the beat is a non-detect beat, a minor beat or a major beat comprises:
    comparing the ST segment shift of the beat to each of a minor threshold and a major threshold;

determining the beat is a non-detect beat if the ST segment shift does not exceed the minor threshold;

determining the beat is a minor beat if the ST segment shift is at or above the minor threshold; and determining the beat is a major beat if the ST segment shift is at or above the major threshold.

3. The method of claim 1 wherein a beat set is declared a non-classified set if the count of non-classified beats reaches a non-classified-beat value before the count of classified beats reaches a classified-beat value.

4. The method of claim 3 wherein the plurality of heart beats is Z, the classified-beat value is Y and the non-classified beat value is Z−Y+1.

5. The method of claim 1 wherein a beat set is declared a major set if the count of classified beats reaches a classified-beat value before the count of non-classified beats reaches a non-classified-beat value, and the count of major beats reaches a major-beat value before either of the count of minor beats and the count of non-detect beats reaches its respective minor-beat value and non-detect beat value.

6. The method of claim 5 wherein:

the plurality of heart beats is Z, the classified-beat value is Y and the non-classified-beat value is Z−Y+1; and the major-beat value is X, the minor beat value is X and the non-detect beat value is Y−X+1.

7. The method of claim 1 wherein a beat set is declared a minor set if the count of classified beats reaches a classified-beat value before the count of non-classified beats reaches a non-classified-beat value, and the count of minor beats reaches a minor-beat value before either of the count of major beats and the count of non-detect beats reaches its respective major-beat value and non-detect beat value.

8. The method of claim 7 wherein:

the plurality of heart beats is Z, the classified-beat value is Y and the non-classified-beat value is Z−Y+1; and the major-beat value is X, the minor-beat value is X and the non-detect-beat value is Y−X+1.

9. The method of claim 1 wherein a beat set is declared a non-detect set if the count of classified beats reaches a classified-beat value before the count of non-classified beats reaches a non-classified-beat value, and the count of non-detect beats reaches a non-detect-beat value before either of the count of major beats and the count of minor beats reaches its respective major-beat value and minor-beat value.

10. The method of claim 9 wherein:

the plurality of heart beats is Z, the classified-beat value is Y and the non-classified-beat value is Z−Y+1; and the major-beat value is X, the minor-beat value is X and the non-detect-beat value is Y−X+1.

11. The method of claim 1 further comprising maintaining a count of major sets, a count of minor sets, a count of non-detect sets and a count of non-classified sets.

12. The method of claim 11 wherein the count of major sets is incremented upon declaration of a major set and is initialized upon declaration of a non-detect set.

13. The method of claim 12 further comprising detecting a major ST episode onset when the count of major sets reaches a nominal value.

14. The method of claim 13 wherein upon declaration of a major ST episode, detecting an ST episode exit when a first number of non-classified sets are declared or a second number of non-detect sets are declared.

15. The method of claim 11 wherein the count of minor sets is incremented upon declaration of a major set or declaration of a minor set, and is initialized upon declaration of a non-detect set.

16. The method of claim 15 further comprising detecting a minor ST episode onset when the count of minor sets reaches a nominal value.

17. The method of claim 16 wherein upon declaration of a minor ST episode, detecting an ST episode exit when a first number of non-classified sets are declared or a second number of non-detect sets are declared.

18. The method of claim 11 wherein the count of non-detect sets is incremented upon declaration of a non-detect set, and is initialized upon declaration of a major set or declaration of a minor set.

19. The method of claim 11 wherein the count of non-classified sets is incremented upon declaration of a non-classified set.

20. The method of claim 1 wherein a non-classified beat corresponds to anyone of a paced beat, a beat outside of a specified heart rate range or a PVC.

21. A device for monitoring ST segments, said device comprising:

a sensor configured to sense electrical cardiac activity over a plurality of heart beats defining a beat set; and a processor configured to:

for each beat in the beat set, determine whether the beat is a non-classified beat or a classified beat;

for each classified beat, determine whether the beat of the ST segment is a non-detect beat, a minor beat or a major beat;

maintain a count of classified beats, a count of non-classified beats, a count of major beats, a count of minor beats, and a count of non-detect beats;

declare the beat set to be one of a non-classified set, a major set, a minor set or a non-detect set based on the relative counts of classified beats, non-classified beats, major beats, minor beats, and non-detect beats.

* * * * *